US008092630B2

(12) United States Patent
Ikegami et al.

(10) Patent No.: US 8,092,630 B2
(45) Date of Patent: Jan. 10, 2012

(54) ABSORBENT ARTICLE FOR ANIMALS AND MANUFACTURING METHOD THEREOF

(75) Inventors: Takeshi Ikegami, Tokyo (JP); Kenji Hiroshima, Tokyo (JP)

(73) Assignee: Uni-Charm Corporation, Ehime (JP)

( * ) Notice: Subject to any disclaimer, the term of this patent is extended or adjusted under 35 U.S.C. 154(b) by 601 days.

(21) Appl. No.: 11/613,398

(22) Filed: Dec. 20, 2006

(65) Prior Publication Data

US 2007/0149941 A1 Jun. 28, 2007

(30) Foreign Application Priority Data

Dec. 22, 2005 (JP) ................. 2005-370839

(51) Int. Cl.
*B32B 37/00* (2006.01)
*B32B 37/02* (2006.01)
*B32B 38/00* (2006.01)
*B32B 38/04* (2006.01)
*A61F 13/15* (2006.01)

(52) U.S. Cl. ........ 156/259; 156/250; 156/252; 156/253; 156/256; 156/269; 156/271; 604/385.09; 604/385.22; 604/385.3; 604/386

(58) Field of Classification Search .................. 156/160, 156/161, 163, 164, 166, 250, 252–254, 256, 156/259–271; 604/385.09, 385.22, 385.3, 604/386

See application file for complete search history.

(56) References Cited

U.S. PATENT DOCUMENTS

| | | | | |
|---|---|---|---|---|
| 4,850,988 A | * | 7/1989 | Aledo et al. ............. | 604/385.21 |
| 5,146,874 A | * | 9/1992 | Vidal ............................ | 119/868 |
| 5,370,634 A | * | 12/1994 | Ando et al. ............... | 604/385.21 |
| 5,399,219 A | * | 3/1995 | Roessler et al. .............. | 156/259 |
| 5,580,411 A | * | 12/1996 | Nease et al. .................. | 156/260 |
| 6,596,107 B2 | * | 7/2003 | Stopher ............................ | 156/66 |
| 2003/0055389 A1 | * | 3/2003 | Sanders et al. ................ | 604/358 |
| 2004/0122413 A1 | * | 6/2004 | Roessler et al. .............. | 604/386 |
| 2007/0129700 A1 | | 6/2007 | Yoshida | |

FOREIGN PATENT DOCUMENTS

| | | |
|---|---|---|
| EP | 0768073 A1 | 4/1997 |
| EP | 1688116 A1 | 8/2006 |
| EP | 1709870 A1 | 10/2006 |
| GB | 2303048 A | 2/1997 |
| JP | 2003-038054 | 2/2003 |
| JP | 2003-047360 | 2/2003 |
| JP | 2003-052267 | 2/2003 |
| JP | 2003-088262 | 3/2003 |
| JP | 2003-102313 | 4/2003 |
| JP | 2004-159591 | 6/2004 |
| JP | 2004-159592 | 6/2004 |
| JP | 2004-194566 | 7/2004 |
| JP | 2005-151869 | 6/2005 |
| JP | 2005160506 A | 6/2005 |
| WO | 2005051276 A1 | 6/2005 |

* cited by examiner

*Primary Examiner* — Philip Tucker
*Assistant Examiner* — Christopher C Caillouet
(74) *Attorney, Agent, or Firm* — Lowe, Hauptman, Ham & Berner, LLP (57) ABSTRACT

A method of manufacturing an absorbent article for animals is provided, wherein U-shaped fixing parts(3,30) are mounted to each side edge of a base material(20) of a diaper main body, and then separated into fixing protrusions(31) along a cutout line(41) to serve as movable parts(21,22), thereby allowing firm tightening to the crural area of hind legs and the trunk.

11 Claims, 12 Drawing Sheets

ABSORBENT ARTICLE FOR ANIMALS AND MANUFACTURING METHOD THEREOF

This application is based on and claims the benefit of priority from Japanese Patent Application No. 2005-370839, filed on Dec. 22, 2005, the content of which is incorporated herein by reference.

BACKGROUND OF THE INVENTION

1. Field of the Invention

The present invention relates to a method of manufacturing absorbent articles for animals, the articles being attached to the lower body thereof. Specifically the invention relates to a method of manufacturing absorbent articles for animals, the articles being capable of being firmly fixed, in particular, to both legs and trunk of quadrupedal animals.

2. Related Art

Conventionally, absorbent articles for animals with elongated bodies are widely available, the articles including a belly facing section applied to the belly of an animal, a back facing section applied to the back of the animal, and an intermediate section located between the belly facing section and the back facing section. For example, a diaper for a pet disclosed in Japanese Published Unexamined Patent Application No. 2004-159591 includes a fastening tape provided to each side edge of the belly facing section, wherein the fastening tapes are fastened and fixed to the back facing section, thus allowing maintenance of the state of the diaper when it was initially attached to a pet.

When the conventional absorbent articles for animals, however, are loose in the crural area of hind legs of a quadrupedal pet, the close contact between the absorbent article and excretory organs of the pet cannot be maintained due to motion of the hind legs, causing leakage of an excretion. In the case of male animals, particularly, sexual organs may protrude from the side of the intermediate section of the absorbent article. In order to cope with such motion of the hind legs of the quadrupedal pet, as distinct from absorbent articles for humans who walk upright, it is important not only to wind and tighten the belly facing section and the back facing section to the trunk of the quadrupedal pet, but also to firmly fix the intermediate section in the vicinity of the crural area of the hind legs. However, no method of manufacturing such absorbent articles for animals has been disclosed yet.

SUMMARY OF THE INVENTION

It is an object of the present invention to provide a method of manufacturing an absorbent article for animals, which includes a fixing part that allows firm tightening of the absorbent article with respect to, particularly, the hind legs of a quadrupedal pet in the vicinity of the crural area and the trunk thereof.

The inventors have devised an absorbent article for animals, which includes a plurality of fixing means or devices arranged at each side edge and allowing suitable tightening to the trunk and the hind legs in the vicinity of the crural area, by using only one transfer device, which is a fastening tape or fixing part with respect to each side edge. Specifically, when manufacturing an absorbent article for animals, which includes a plurality of fixing means or devices, the inventors have decided to include, in a method of manufacturing an absorbent article for animals, a process of mounting in advance a fixing part having a plurality of fixing protrusions or a process of separating a mounted fixing part into a plurality of fixing protrusions. More specifically, the present invention provides the following manufacturing method.

In a first aspect of the present invention, there is provided a method of manufacturing an absorbent article for an animal, the absorbent article including a fixing device for fixing a belly facing section applied to the belly of the animal and a back facing section applied to the back of the animal when the absorbent article is attached to the animal, the method including the steps of: mounting a fastening member to an elongated tape base material; cutting the tape base material into separate and distinct fixing parts so as to provide at least two fixing protrusions in a region of the tape base material in which the fastening member is mounted; and mounting at least one fixing part to one of each side edge of the belly facing section, each side edge of the back facing section, and each side edge of a sheet base material serving as a material of the belly facing section or the back facing section.

According to the first aspect of the present invention, the fixing part constituting a fixing device for fixing an absorbent article at the time of attachment is manufactured to include in advance a plurality of protrusions having a fastening member. As a consequence, by merely mounting the fixing part to a main body or material of the absorbent article, the absorbent article can be manufactured having a plurality of fixing protrusions at each side edge. Due to the fixing protrusions, suitable fixing can be made at various areas of the body of the animal, e.g., at the crural area and trunk when two fixing protrusions are provided.

In a second aspect of the present invention, the fixing protrusions of the fixing part are in a pair, wherein the method further includes the step of cutting out a portion of the belly facing section, back facing section, and sheet base material, having the fixing part mounted thereto together with the fixing part or independently thereof.

According to the second aspect of the present invention, a pair of fixing protrusions is provided, at two side edges, and part of the main body or material of the absorbent article mounted between the pair of fixing protrusions is also cut out. Therefore, when attaching the absorbent article, the fixing protrusions can be fixed by moving part of the absorbent article that forms a base of the fixing protrusions, having increased movable range.

In a third aspect of the present invention, there is provided a method of manufacturing an absorbent article for an animal, the absorbent article including a fixing device for fixing a belly facing section applied to a belly of the animal and a back facing section applied to a back of the animal when the absorbent article is attached to the animal, the method including the steps of: mounting a fastening member to an elongated tape base material; cutting the tape base material into separate and distinct fixing parts, formed of a continuum of the tape provided with the fastening member; mounting at least one fixing part to one of each side edge of the belly facing section, each side edge of the back facing section, and each side edge of a sheet base material serving as a material of the belly facing section or the back facing section; and cutting and separating the mounted fixing part into a plurality of fixing protrusions.

According to the third aspect of the present invention, when arranging the fixing device, without mounting a plurality of fixing protrusions as formed initially separately to a main body of the absorbent article, continuous belt-like fixing parts are first mounted, which are then cut and separated into a plurality of fixing protrusions. As a consequence, there is no need to carry out mounting of the fixing protrusions at multiple times or locations, resulting in no need to frequently set the number of times of mounting or positional adjustment.

Moreover, by carrying out cutting into the fixing protrusions concurrently with another cutting process of forming the absorbent article, e.g., a cutting process of forming the leg openings, a suitable absorbent article can be manufactured without any extension of manufacturing time compared to the conventional art.

The shape and state of the fixing protrusion are not particularly limited. The fixing protrusion may be rectangular and concavo-convex at the stage of the fixing part on condition that the shape and state allow separation into a plurality of fixing protrusions after being mounted to the main body or material of the absorbent article.

In a fourth aspect of the present invention, the cutting and separating step includes cutting out a portion of the fixing part along a substantially U-shaped cutout line.

According to the fourth aspect of the present invention, at the stage of separating the fixing part into the fixing protrusions, the fixing part is not cut simply linearly, but in a U-shape. With this, the movable range of the fixing protrusions is increased, allowing free setting of the direction and strength of tightening of the fixing protrusions at the time of attachment. Moreover, the fixing protrusions can be shaped so that a handler has an easy grasp of the fixing protrusions at the time of attachment. It is noted that, according to a fifth aspect of the present invention as will be described later, such a portion to be cut out can be reduced, avoiding waste of the tape base material as a raw material.

In a fifth aspect of the present invention, the fastening member mounting step includes cutting, so as to form a concave shape, the tape base material, that is fabricated to have a constant width, and to have the fastening member, that has an elongated shape, extending in a longitudinal direction of the tape base material in a central portion of the width of the tape base material, wherein the cutting step includes: a first cutting process of cutting the tape base material along a cyclic-wave curve with peaks and valleys having an amplitude greater than a width of the fastening member and extending continuously in the length direction; and a second cutting process of cutting the tape base material in a direction from one edge towards whichever of a crest of a peak or a bottom of a valley is farther away, and from another edge towards whichever of a crest of a peak or a bottom of a valley is farther away, so as to obtain separate and distinct fixing parts serving as fastening tapes.

According to the fifth aspect of the present invention, the fixing part is formed in a concave shape prior to the mounting process of the absorbent article. Specifically, two portions serving as suitable holding and fastening parts when the absorbent article is attached are formed in advance. Moreover, by arranging a cutout portion in a concave shape concavity in the separation process, the fixing protrusions can be shaped so that a handler has an easy grasp of the fixing protrusions when a handler attaches an absorbent article to an animal. Furthermore, the distance is greater between the fixing protrusions formed of one fixing part due to presence of the concavity, resulting in increased movable range of the fixing protrusions. Furthermore, the tape base material is cut with the concavities engaged with each other, avoiding waste of the tape base material.

In a sixth aspect of the present invention, the method further includes the step of adjusting timing of the second cutting process so as to allow individual adaptation of the fixing device of the absorbent article to target animals.

According to the sixth aspect of the present invention, by adjusting timing for cutting the tape base material in the second cutting process, the size of the fixing protrusions to be formed can be changed. For example, when the strength of fixing about the hind legs needs to be increased, a cut timing is set to increase the size of the rearward fixing protrusion with respect to the direction of travel of the tape base material. This allows smaller formation of the protrusion serving as a forward fixing protrusion for fixing the absorbent article about the trunk and greater formation of the protrusion serving as a rearward fixing protrusion for fixing the absorbent article about the crural area of the hind legs.

In a seventh aspect of the present invention, the cutting and separating step comprises cutting out a portion of the side edge of the belly facing section or back facing section having the fixing part mounted thereto, the portion being equal to or greater than the portion of the fixing part as cut out.

According to the seventh aspect of the present invention, not only the fixing part, but also part of the absorbent article having fixing protrusions mounted thereto are cut out. With this, not only the fixing protrusions, but also a portion having fixing protrusions mounted thereto can be moved at the time of attachment, resulting in achievement of more suitable attachment of the absorbent article. Moreover, there is no need to arrange a separate and distinct movable part having such an effect in the manufacturing process of the absorbent article, allowing easy formation of a movable part with a simple method. A portion to be cut out may be either only a portion in which the fixing part is mounted or a portion greater than the portion in which the fixing part is mounted. In this connection, in the latter case in which a greater portion is cut out, the movable part can further be increased, resulting in further increase in movable range of the fixing protrusions in attachment operation. With this, a handler easily carries out fixing of an absorbent article adapted to a target animal in the attached state of the absorbent article.

In an eighth aspect of the present invention a dimension of the fixing part from the belly facing section to the back facing section is 40 to 200 mm at both ends of the belly facing section, the back facing section, or the sheet base material serving as a material of the belly facing section or the back facing section.

According to the eighth aspect of the present invention, the width of the fixing part is as described above in the finished state of an absorbent article, i.e., state after forming the fixing protrusions and the movable part. As a consequence, an inconvenience and/or difficulty may not occur when attaching the absorbent article to a target animal, such as inconvenient attachment operation due to unnecessarily large size of the fixing part and difficult attachment due to the size of the fixing part being too small to carry out necessary fastening.

In a ninth aspect of the present invention, there is provided an absorbent article for an animal, comprising: a belly facing section applied to a belly of the animal when worn; a back facing section applied to a back of the animal when worn; and a fixing device that fixes the belly facing section and the back facing section when worn, the fixing device being arranged at each side edge of one of the belly facing section and the back facing section, the fixing device being of an oblong shape having a length direction and a width direction, the fixing device having, in the length direction, one end formed with a pair of fixing protrusions and, in the width direction, at least one end formed with a fixing part having a substantially linear shape.

According to the ninth aspect of the present invention, at least one end of the fixing part is formed substantially linearly. For example, when only one end of the fixing part is formed substantially linearly (refer to FIGS. 9 and 10), the other end is not formed substantially linearly, and thus includes an unnecessary portion. On the other hand, the one end is formed substantially linearly, and thus includes little or no unnecessary portion, so that the fixing part can be mounted with the one end being arranged substantially along a front or rear end of the absorbent article in the length direction. Specifically, on one hand, when an end of the fixing part in the width direction includes a large unnecessary portion at the front or rear end of the absorbent article, the fixing part should be mounted inside by the dimension of the unnecessary portion. On the other hand, the one end of the fixing part includes little or no unnecessary portion, allowing mounting of the fixing part without requiring delicate positional adjustment.

In a tenth aspect of the present invention, both ends of the fixing part in the width direction have a linear shape.

According to the tenth aspect of the present invention, the fixing part has both ends formed linearly in the width direction. As a consequence, both ends of the fixing device of the finished absorbent article include no unnecessary portions, which is preferable functionally and allows material savings. When mounting the fixing part to the main body or material of the absorbent article, the mounting position of the fixing part is not restricted due to the absence of unnecessary portions at both ends, facilitating adjustment of the mounting position of the fixing part. Such an absorbent article can be manufactured by the manufacturing method described in any one of the third or the seventh aspects of the present invention, wherein the fixing part can be manufactured at the time of cutting in the second cutting process in which the cut portion is formed linearly.

In an eleventh aspect of the present invention, the fixing part is cut between the pair of fixing protrusions.

According to the eleventh aspect of the present invention, the fixing part is cut between the pair of fixing protrusions, obtaining increased movable range of the fixing protrusions. The absorbent article including such fixing part can be manufactured, particularly, by the manufacturing method described in the fourth and seventh aspects of the present invention.

As described above, according to the present invention, an absorbent article for animals that allows suitable achievement of fixing of the belly facing section and the back facing section at a plurality of areas can be manufactured without complicating the conventional manufacturing process or increasing manufacturing time. Moreover, by the simple method of adjusting the timing for cutting the base material of a fixing member, individual adaptation of the absorbent article to target animals can be obtained. Furthermore, the present invention can provide an absorbent article for animals including no unnecessary portion at one end or both ends of the fixing part constituting a fixing device.

DETAILED DESCRIPTION OF THE INVENTION

Referring to the drawings, the embodiments of the present invention are described hereafter. It is noted that, in the description about the embodiments other than the first embodiment, like references are assigned to parts common to those in the first embodiment, the explanation of which is omitted or simplified.

First Embodiment

Fundamental Configuration

Figure 1:
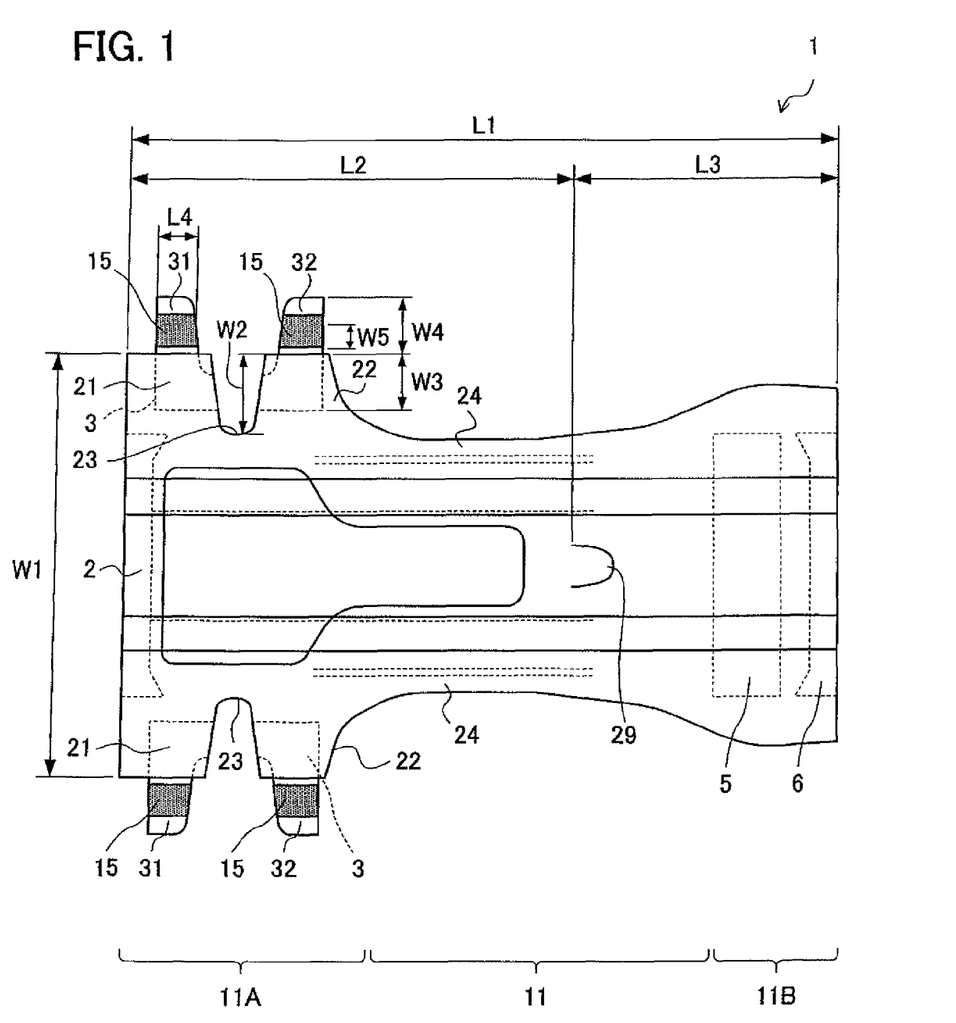
FIG. 1 is a plan diagram showing a diaper for pets manufactured by a first embodiment of a manufacturing method, as viewed from the body contact side.
Figure 2:
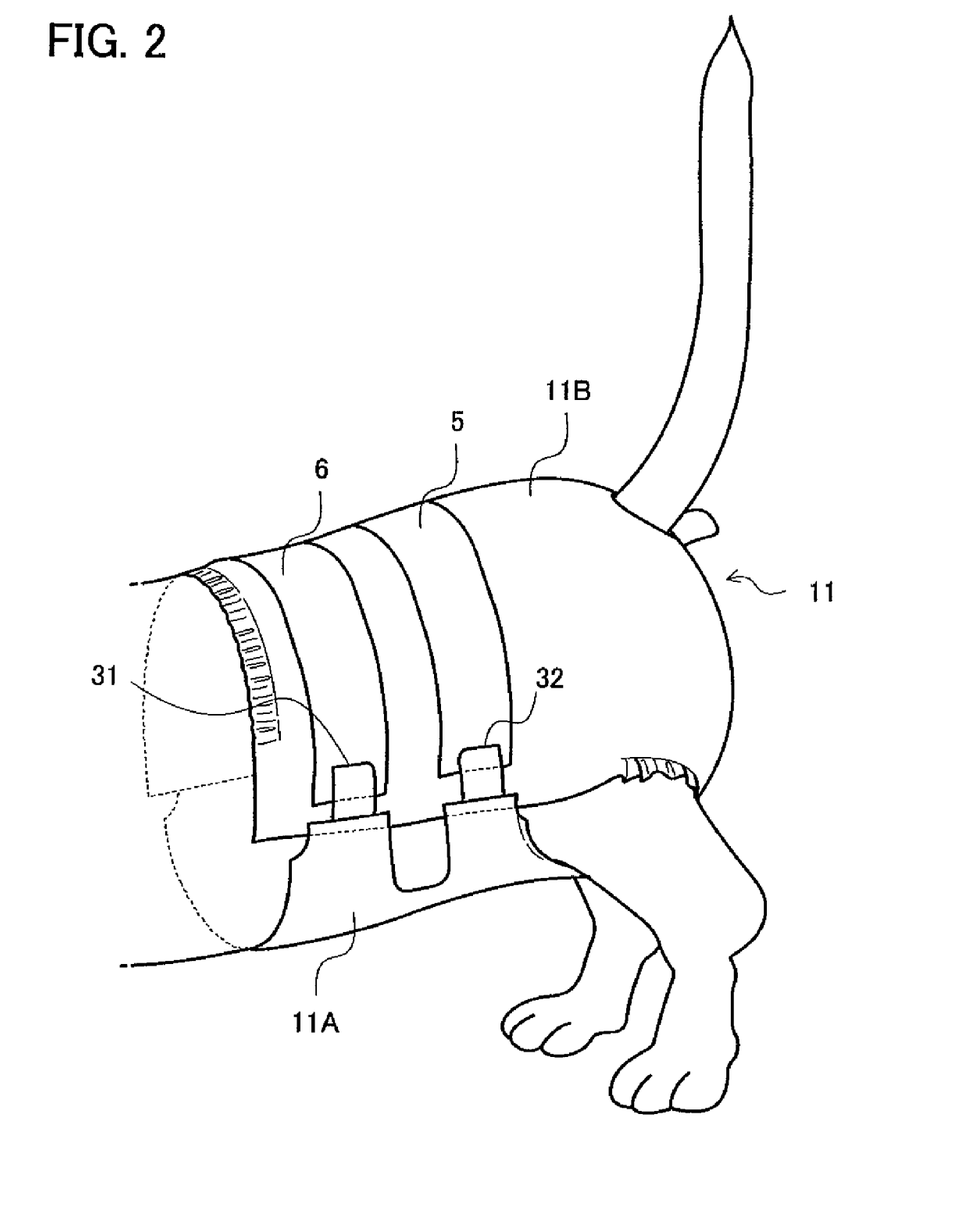
FIG. 2 is a diagram showing a state in which the diaper according to the first embodiment is attached.
Figure 3:
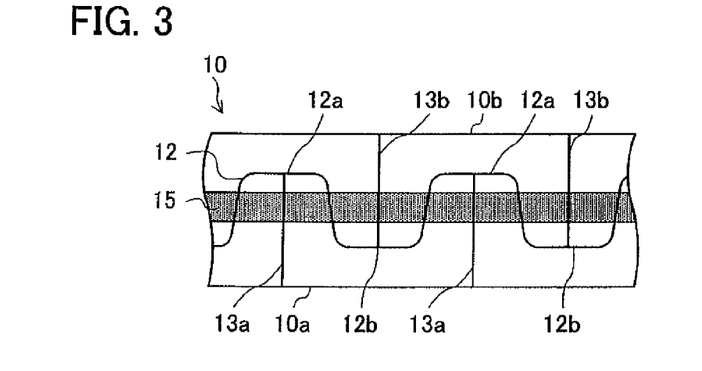
FIG. 3 is a diagram showing a portion of a fastening-tape base material to be cut in the first embodiment of the manufacturing method.
Figure 4:
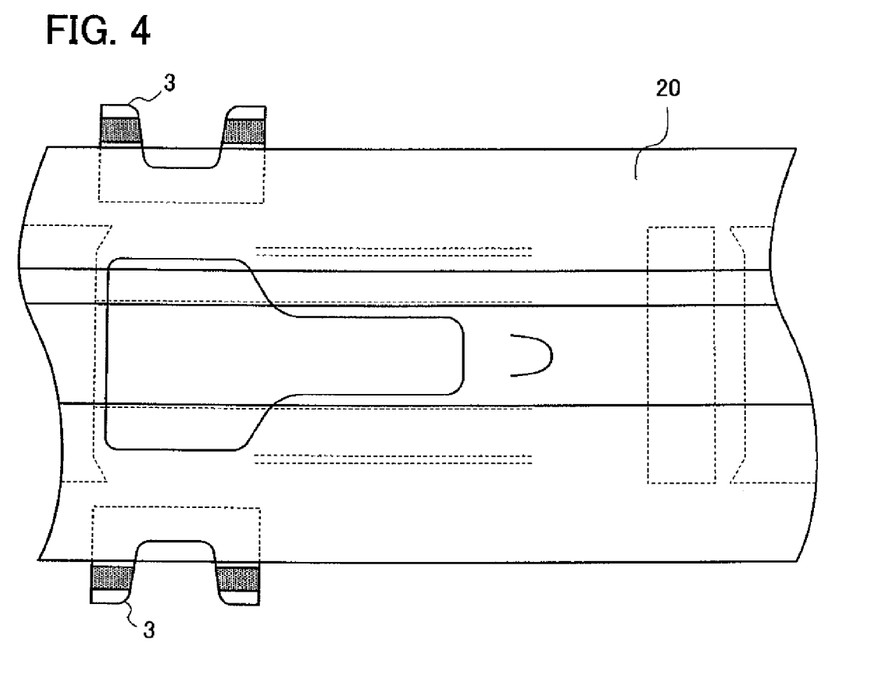
FIG. 4 is a diagram showing a state in which fixing parts are affixed to a diaper main-body base material in the first embodiment of the manufacturing method.
Figure 5:
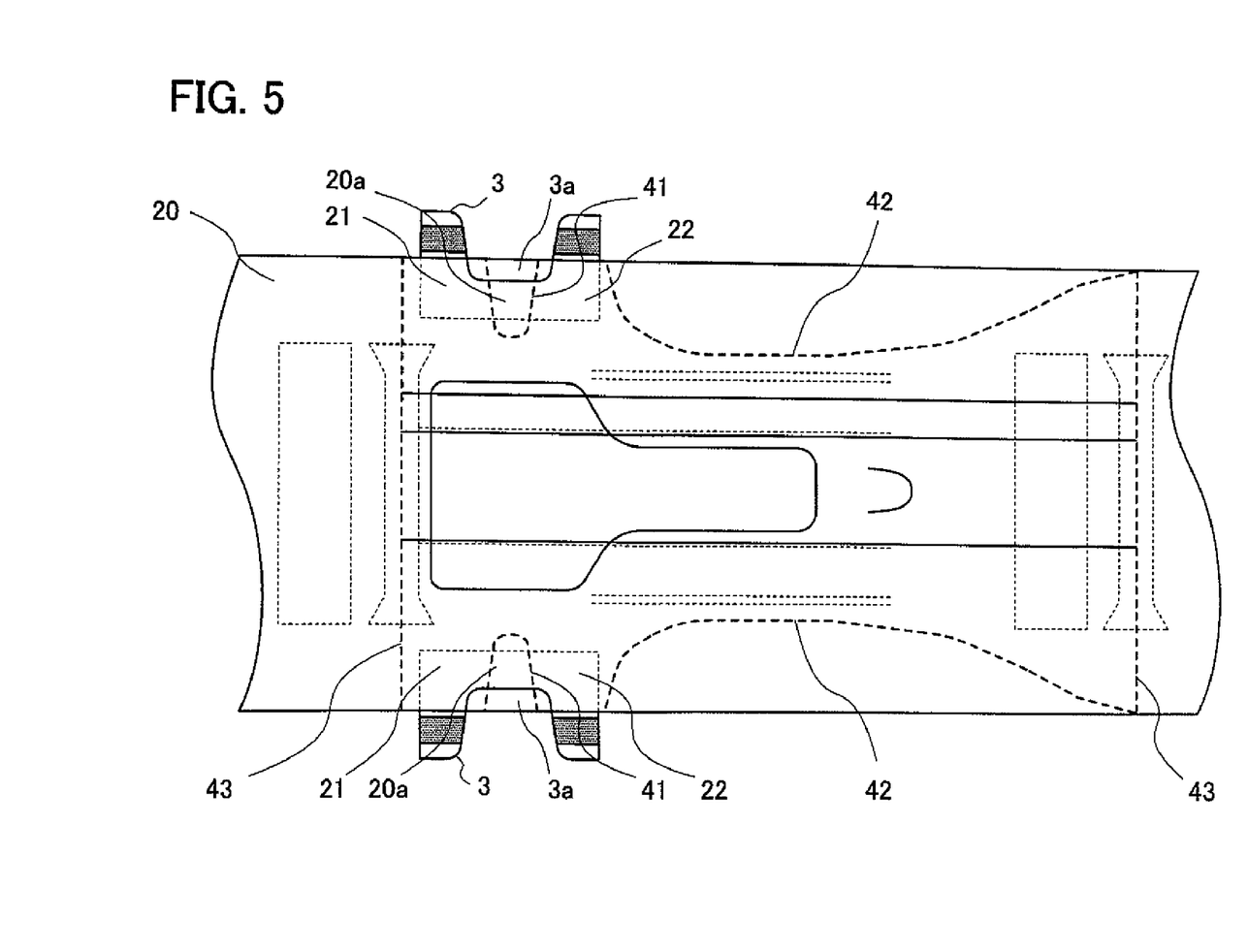
FIG. 5 is a diagram for explaining portions to be cut out of the base materials of the fixing part and diaper main body in the first embodiment of the manufacturing method.
Figure 6:
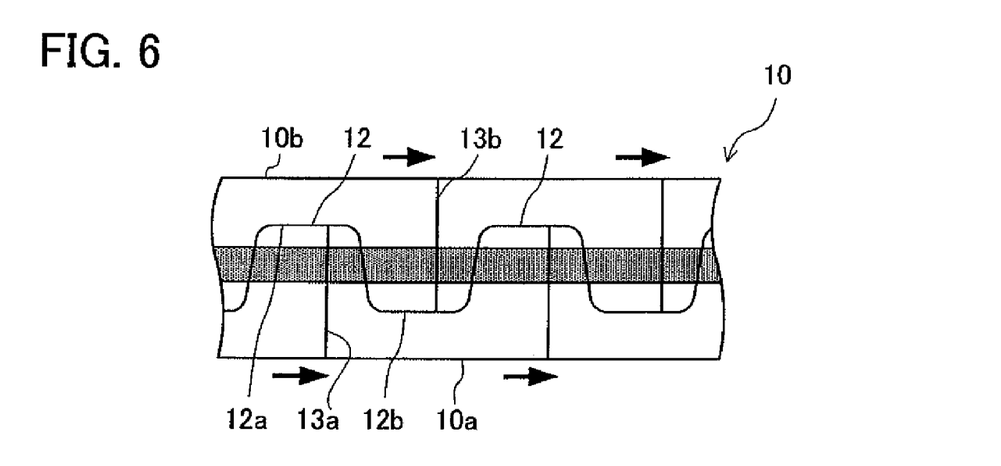
FIG. 6 is a diagram showing a different cutting position of the fastening-tape base material in the first embodiment of the manufacturing method.
Figure 7:
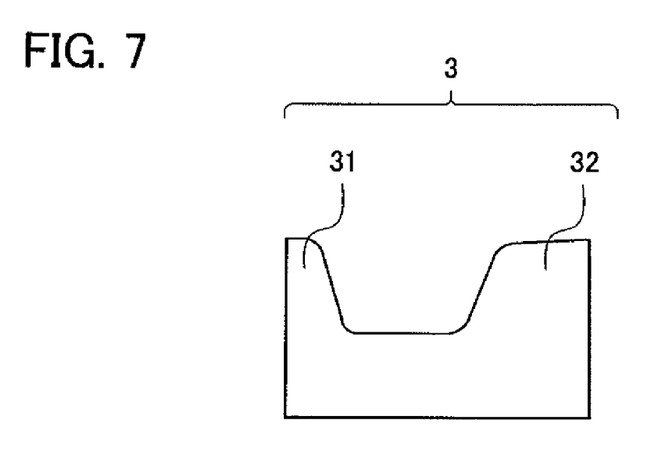
FIG. 7 is a schematic diagram showing the fixing part cut along cutting lines shown in FIG. 6.

FIG. 1 is a plan diagram showing a diaper for pets or an absorbent article for animals, which is manufactured by a manufacturing method of the present invention, as viewed from the body contact side. FIG. 2 is a diagram showing a state in which the diaper is attached. FIG. 3 is a diagram for explaining a portion of a fastening-tape base material to be cut, which is a material of a fixing part mounted on the diaper. FIG. 4 is a diagram showing a state in which the fastening tapes or fixing parts as cut separately are affixed to a diaper main-body base material. FIG. 5 is a diagram for explaining portions to be cut out of the base materials of the fixing part and diaper main body. FIG. 6 is a diagram showing a case in which the cutting lines for cutting the fastening-tape base material are arranged in a different position. FIG. 7 is a schematic diagram showing the fixing part cut along the cutting lines shown in FIG. 6.

Referring to FIG. 1, a diaper 1 for pets includes three sections, i.e., an intermediate section 11, a belly facing section 11A, and a back facing section 11B, the belly facing section 11A and back facing section 11B being continuously arranged on the left and right of the intermediate section 11. Referring to FIG. 2, when attaching the diaper 1, the intermediate section 11 is mainly attached to hind legs of an animal in the vicinity of the crural area, the belly facing section 11A is applied to the belly of the animal in front of the crural area, and the back facing section 11B is applied to the back of the animal in front of the crural area. In order to secure the state of the intermediate section 11, belly facing section 11A, and back facing section 11B applied to the body of the animal, fixing protrusions 31 and fixing protrusions 32 affixed to a main body 2 of the diaper 1 are fastened to a joining tape 6 and a joining tape 5, respectively.

As shown in FIG. 1, the fixing protrusions 31 are fixed to movable parts 21 located at both side edges in the length direction by affixing. The fixing protrusions 32 are fixed to movable part 22 by attaching. The fixing protrusions 31 and 32 can be bent and deformed freely and independently due to presence of a recess 23. As a consequence, the fixing protrusions 31 and 32 can be fastened suitably to the joining tapes 5 and 6 according to the shape of a target animal.

As for the dimensions of the diaper 1, length L1 is 530 mm, width W1 is 320 mm, dimension L2 from an end of the back facing section 11B to an end of a U-shaped tear-off line 29 for insertion of a tail is 350 mm, and dimension L3 from the belly facing section 11A to the end of the tear-off line 29 is 180 mm. Moreover, length W2 of the movable parts 21 and 22 is 45 mm, dimension W3 of a mounting of a fixing part 3 in the movable parts 21 and 22 is 38 mm, length W4 of the fixing protrusions 31 and 32 is 38 mm, length W5 of a fastening member 15 is 28 mm, and width L4 of the fastening member 15 is 27.5 mm.

Manufacturing Method

The fixing protrusions 31 and 32, which are not originally separate and distinct members, are separated in the manufacturing process. Specifically, referring to FIG. 3, first, the fastening member 15 that can be fastened to the joining tapes 5 and 6, not shown, is affixed to a long fastening-tape base material 10 serving as a base material of the fixing part 3. Then, in a first cutting process, the fastening-tape base material 10 serving as a base material of the fastening part 3 is cut in the length direction. The first cutting process is a process in which the fastening-tape base material 10 is cut in the length direction along an undulant cyclic-wave curve 12 with peaks and valleys arranged to cross the fastening member 15 and extending continuously in the length direction. Subsequently, in a second cutting process, the fastening-tape base material 10 as cut in the length direction is cut in the width direction. The second cutting process is a process in which the fastening-tape base material 10 as cut in the length direction in the first cutting process is cut along a cutting line 13a extending from a lower edge 10a to a crest 12a of the peak and along a cutting line 13b extending from an upper edge 10b to a bottom 12b of the valley, obtaining separate and distinct fixing parts 3. With this, U-shaped fixing parts or fastening tapes 3 are formed. Referring to FIG. 4, the fixing parts 3 are mounted to a base material 20 of the diaper main body 2 in predetermined positions. A protrusion of the fixing part 3 may be folded back to the base material 20 like in the third embodiment as will be described later.

Next, the fixing part 3 is formed at the fixing protrusion. This operation is carried out with the fixing part 3 mounted to the diaper main-body base material 20. Referring to FIG. 5, first, an unnecessary portion 3a of the fixing part 3 is cut out. With this, the fixing part 3 is separated into pair of fixing protrusions 31 and 32. When cutting out the unnecessary portion 3a of the fixing part 3, in addition to the unnecessary portion 3a of the fixing part 3, an unnecessary portion 20a of the base material 20 to which the fixing part 3 is fixed is also cut out. Specifically, the fixing part 3 and base material 20 are cut out along a cutout line 41. With this, the fixing part 3 is separated into the fixing protrusions 31 and 32, and a recess 23 is formed in the base material 20, forming the movable parts 21 and 22 in a suitable shape. The unnecessary parts as cut out are retrieved by air suction or the like. This cutout process can be carried out more efficiently when performed concurrently with the process of cutting out the base material 20 along cutout lines 42 for forming leg openings 24 shown in FIG. 1. Then, the base material 20 is cut in the width direction along a cutoff line 43, obtaining separate and distinct diaper 1.

The manufacturing method of pair of fixing projections 31 and 32 is not limited to the above-mentioned method in which the fixing part 3 is affixed to the diaper main-body base material 20 and then separated into the fixing protrusions 31 and 32. Optionally, two originally separate and distinct fixing protrusions may be affixed to the diaper main-body base material 20. However, when adopting the alternative of affixing two originally separate and distinct fixing protrusions, affixing is carried out by arranging tape transfer devices with respect to the respective fastening tapes, so that two tape transfer devices are needed at each side edge of the diaper main-body base material 20. That is, twice the amount of equipment such as a tape cutter, tape transfer device, has to be provided as compared to the first embodiment. This results in occurrence of the problem of complicated manufacturing as well as increased cost of capital investment. In this connection, according to the manufacturing method in the first embodiment, the conventional equipment is used in which, while adjusting the feed of the fastening-tape base material 10 serving as a base material of the fixing part 3, the fastening-tape base material is cut along the undulant cyclic-wave curve 12, forming the fixing parts 3. The fixing part 3 is cut in the cutting process of the diaper main-body base material 20. With this, the diaper 1 having two fixing protrusions can be manufactured, resulting in curtailment of the manufacturing process and capital investment.

Individual Adaptation to Target Animals

According to the first embodiment described above, the fixing protrusions 31 and 32 are formed to provide a shape of substantially mirror symmetry. Optionally, by changing the timing for cutting the fastening-tape base material 10 in the width direction, individual adaptation of the fixing protrusions 31 and 32 to the shape of target animals can be obtained. For example, referring to FIG. 6, the cutting line 13a for cutting the fastening-tape base material 10 in the width direction is arranged in the position of the crest 12a of the cyclic-wave curve 12 slightly shifted to the bottom 12b in the direction of travel, in place of being arranged in the center of the crest 12a as shown in FIG. 3. Likewise, the cutting line 13b is arranged in the position of the bottom 12b slightly shifted to the crest 12a in the direction of travel, in place of being arranged in the center of the bottom 12b. With this, referring to FIG. 7, the fixing part 3 can include a greater protrusion serving as a fixing protrusion 32 located on the side of the legs, which may be used in diapers suitable for animals requiring higher adhesion strength about the legs. Thus, by changing the cut timing in the cutting process as appropriate, individual adaptation of the fixing protrusions 31 and 32 to the target animals can be obtained.

Second Embodiment

Figure 8:
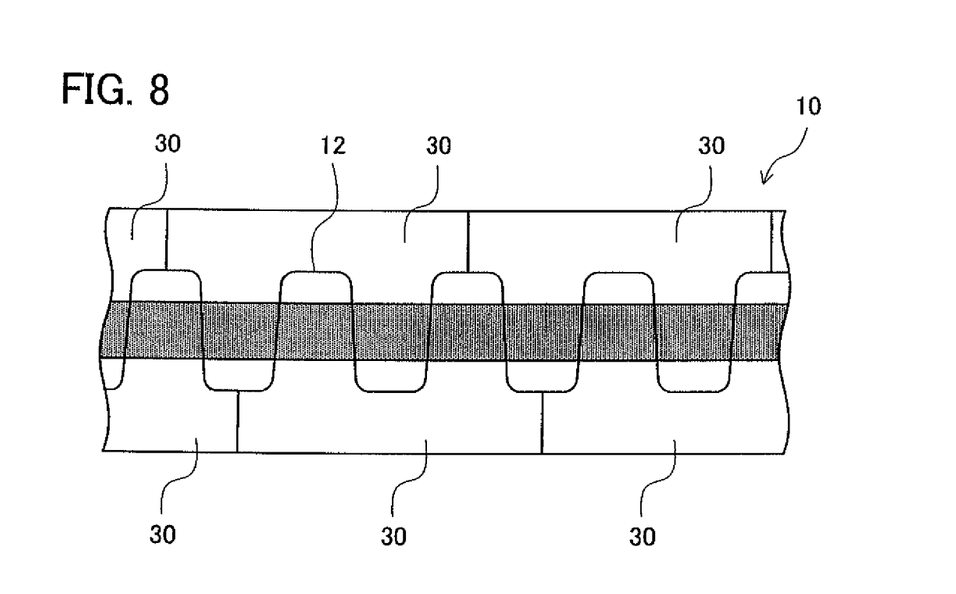
FIG. 8 is a diagram for explaining a cutting method of the fastening-tape base material according to a second embodiment.
Figure 9:
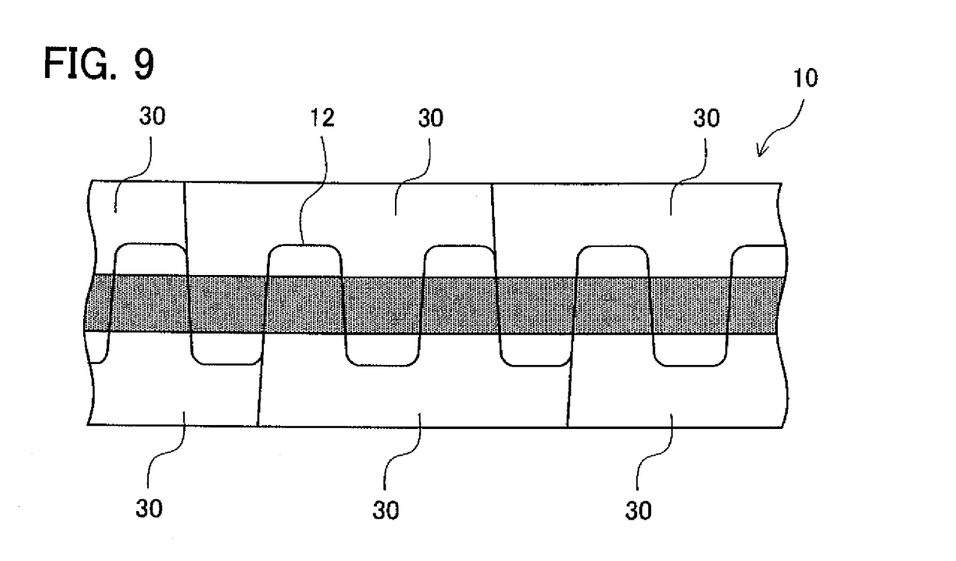
FIG. 9 is a diagram showing another example of cutting lines in the second embodiment.
Figure 10:
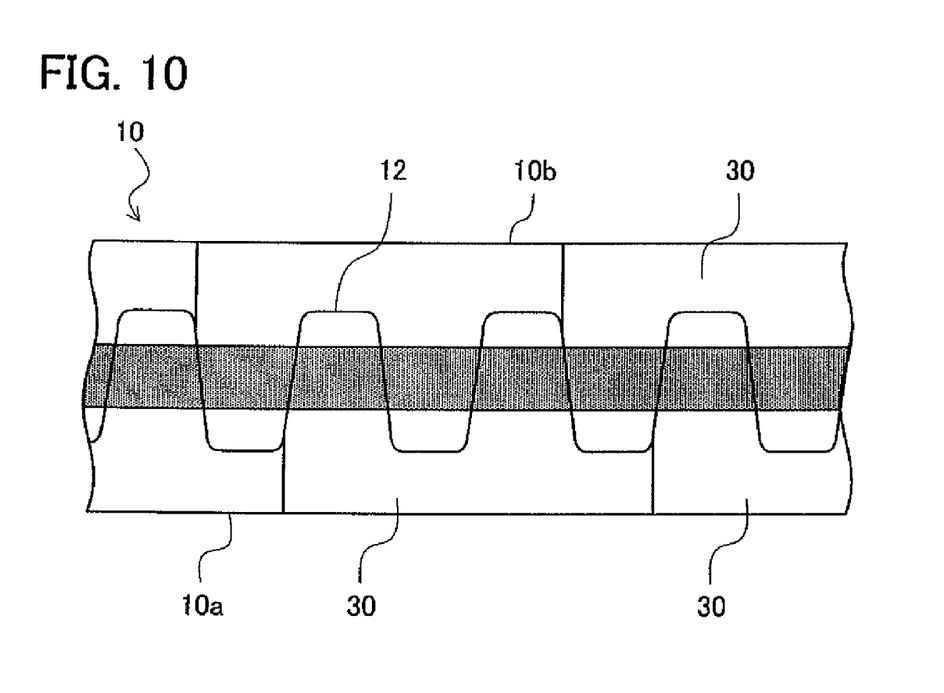
FIG. 10 is a diagram showing still another example of cutting lines in the second embodiment.

Next, the second embodiment is described. FIG. 8 is a diagram for explaining a cutting method according to the second embodiment, and FIGS. 9 and 10 are diagrams for explaining the cutting lines in the second embodiment.

When cutting the fastening-tape base material 10 as shown in FIG. 8, a pair of fixing protrusions is already provided at the moment that a fixing part 30 is formed. Therefore, by merely mounting the fixing part 30 to the diaper main-body base material 20, two fixing protrusions are arranged at each side edge of the diaper 1.

The cutting lines may be formed so that two fixing protrusions are included in one fixing part 30. For example, referring to FIG. 8, the cutting line may extend from the upper edge or lower edge of the fastening-tape base material 10 to the center of the crest or bottom of the cyclic-wave curve 12. Alternatively, referring to FIG. 9, the cutting line may extend from the upper edge or lower edge to the trailing edge or leading edge of the cyclic-wave curve 12 along the extension of the upper edge or lower edge. Optionally, referring to FIG. 10, the cutting line may extend from the upper edge 10b or lower edge 10a to the trailing edge or leading edge of the cyclic-wave curve 12 to be orthogonal to the upper edge 10b or lower edge 10a. In the option shown in FIG. 10, the cutting lines do not extend linearly, but in a dogleg manner. When the cutting lines are formed as shown in FIGS. 9 and 10, one end of one fixing part 30 in the length direction extends substantially linearly.

Comparison between the First and Second Embodiments

Figure 11:
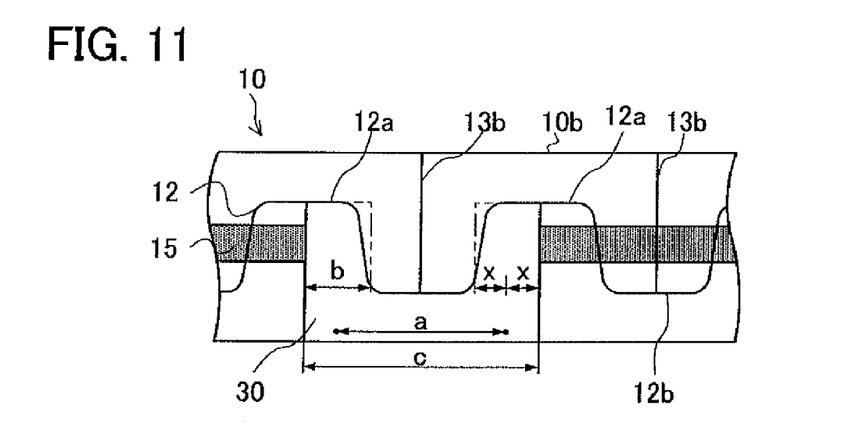
FIG. 11 is a diagram showing the first embodiment for making a comparison with the second embodiment.
Figure 12:
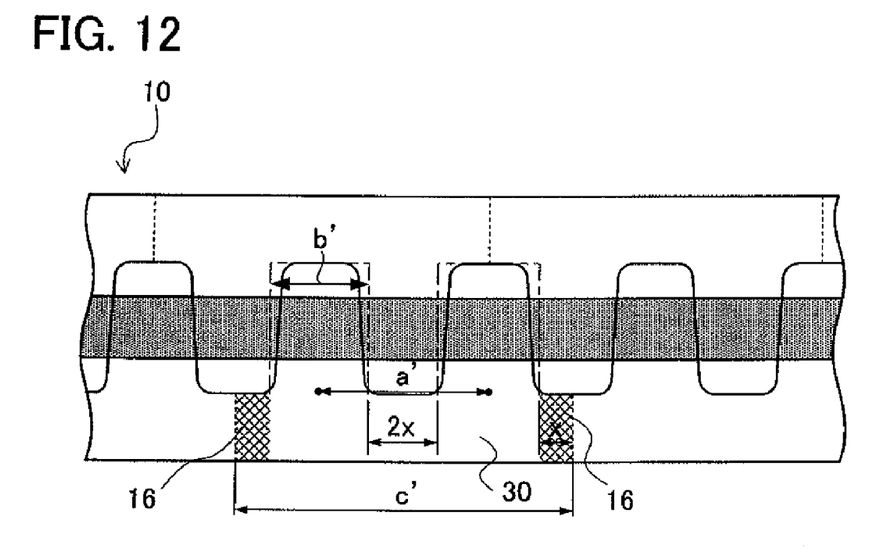
FIG. 12 is a diagram showing the second embodiment for making a comparison with the first embodiment.

Next, a comparison is made between the first and second embodiments. FIG. 11 is a diagram for explaining the first embodiment, and FIG. 12 is a diagram for explaining the second embodiment.

A comparison is described between the first embodiment (wherein cutting is carried out to bisect the crest 12a as shown in FIG. 3, which is not an instance shown in FIG. 6) and the second embodiment. The dimension of the fixing part 3 (30) is determined as appropriate in accordance with the size of the target animals, wherein a fulcrum-to-fulcrum distance a shown in FIG. 11 and a fulcrum-to-fulcrum distance a' shown in FIG. 12 serve as a criterion of determination of the dimension. Suppose that the length of one fixing part 3 (30) in the width direction is c (c'), and the width of one crest or protrusion of the fixing part 30 is b (b'). Suppose that the fulcrum-to-fulcrum distance is a criterion A, the first embodiment can be expressed as follows:

Fulcrum-to-fulcrum distance: $a=4x+x+x=6x=A (x=A/6)$

Width of fixing protrusion: $b=2x=A/3$

Dimension of fixing part: $c=8x=4A/3$

Likewise, suppose that the fulcrum-to-fulcrum distance a' shown in FIG. 12 is criterion A like the fulcrum-to-fulcrum distance a shown in FIG. 11, the second embodiment can be expressed as follows:

Fulcrum-to-fulcrum distance: $a'=4x=A (x=A/4)$

Width of fixing protrusion: $b'=2x=A/2$

Dimension of fixing part: $c'=8x=2A$

Comparing the two, since the dimension of the fixing part in the width direction is 4A/3 in the first embodiment and 2A in the second embodiment, the first embodiment is advantageous in material savings by 2A/3. Specifically, in order to create the fulcrum-to-fulcrum distance A, the manufacturing method in the second embodiment needs a material 1.5 times (2A÷4A/3=1.5) as much as the manufacturing method in the first embodiment. On the other hand, the first embodiment is narrower in the width of the crest or protrusion, which is A/3 in the first embodiment and A/2 in the second embodiment.

However, by setting a shearing force at 30 N or more and the length c of one fixing part 30 in the width direction at 40 to 200 mm, the narrower width of the fixing protrusion does not have a bad influence on adhesion at the time of attachment.

According to the first embodiment, by adjusting the cutting width of the crest or protrusion as described above, adaptation of the fixing protrusions to the type of target animals can be obtained in accordance with the required strength of attachment corresponding to the animals. On the other hand, according to the second embodiment, such adaptation cannot be obtained. Moreover, the first embodiment produces no needless portion at the side of the fixing protrusion (refer to an area 16 shown in FIG. 12), which is inevitably formed in the second embodiment. As a consequence, when mounting the fixing part 3 to the diaper main-body base material 20, the mounting position of the fixing part 3 is not restricted since there is no unnecessary portion.

As described above, when making a comparison between the first and second embodiments, it can be said that the fixing-part forming method of the first embodiment is preferable to that of the second embodiment.

Third Embodiment

Figure 13:
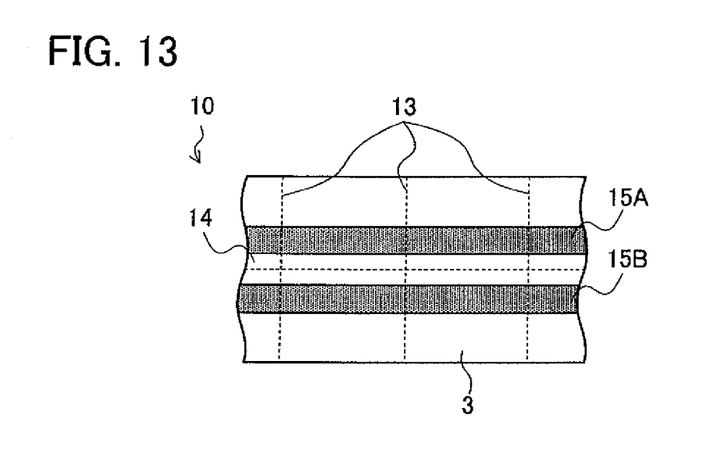
FIG. 13 is a diagram for explaining a cutting method of the fastening-tape base material according to a third embodiment.
Figure 14:
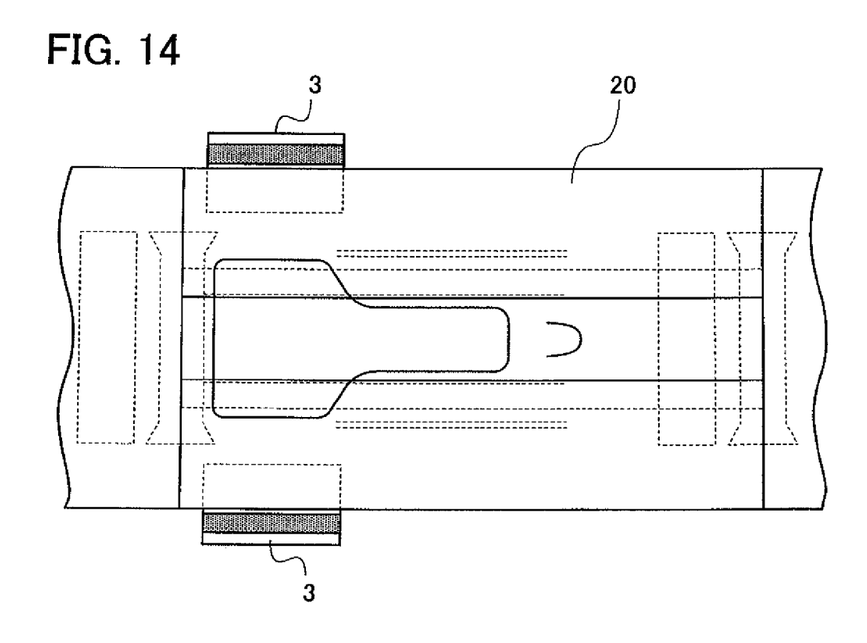
FIG. 14 is a diagram showing a state in which the fixing part separated in FIG. 13 is affixed to the diaper main-body base material.
Figure 15:
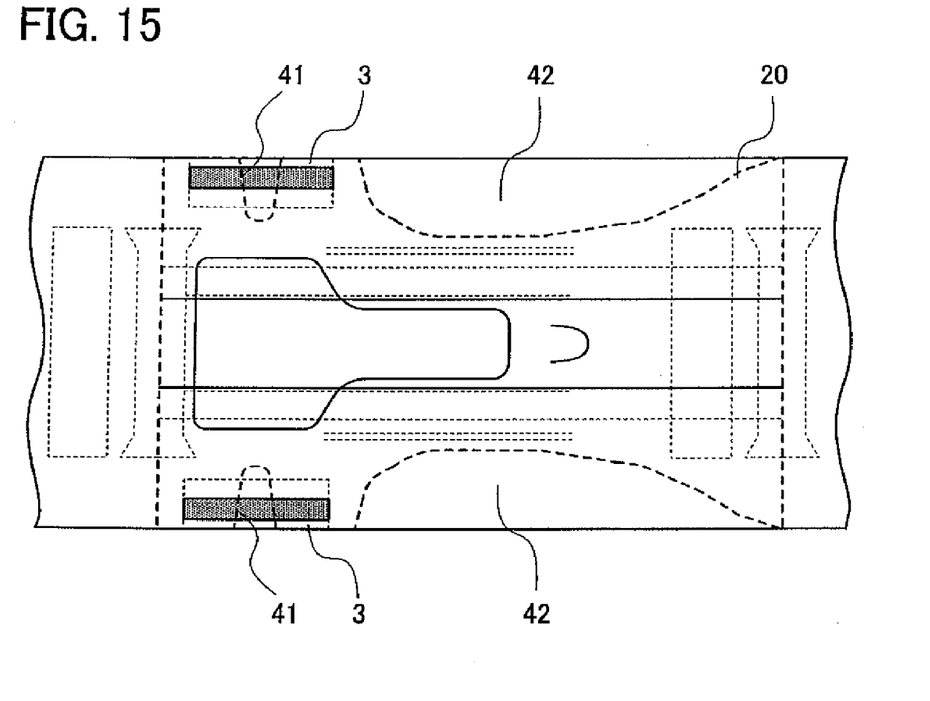
FIG. 15 is a diagram for explaining a method and location in which the fixing part in the third embodiment is cut.
Figure 16:
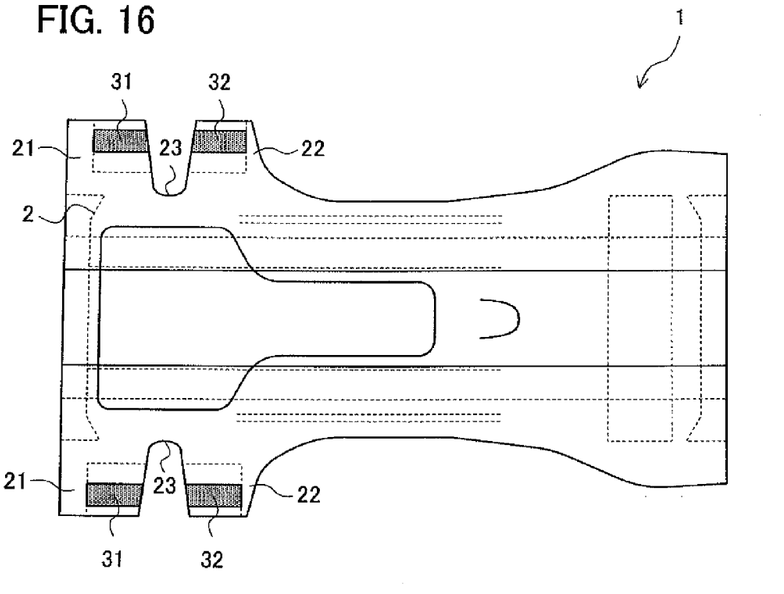
FIG. 16 is a diagram showing a state in which the fixing part and the diaper main-body base material in the third embodiment are cut out.
Figure 17:
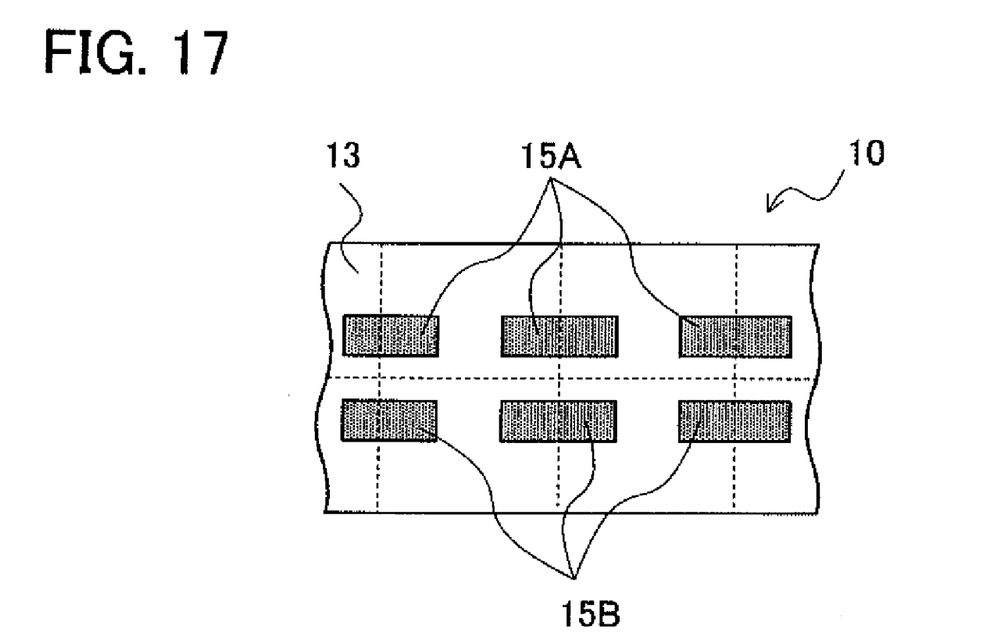
FIG. 17 is a diagram showing another example of a method of mounting a fixing member to the tape base material in the third embodiment.

FIG. 13 is a diagram for explaining a cutting method of the fastening-tape base material according to the third embodiment. FIG. 14 is a diagram showing a state in which the fixing part as separated is affixed to the diaper main-body base material. FIG. 15 is a diagram for explaining a method and location in which the fixing part is cut. FIG. 16 is a diagram showing a state in which the fixing part and the diaper main-body base material are cut out. FIG. 17 is a diagram showing another example of a method of mounting a fixing member to the tape base material.

Referring to FIG. 13, base materials 15A and 15B of the fastening member 15 are affixed to the tape base material so as to obtain fastening-tape base material 10. Then, the fastening-tape base material 10 is cut along a cut line 14 having a predetermined length and cutting lines 13 having a predetermined width therebetween to obtain separate and distinct fixing parts or fastening tapes. Referring to FIG. 14, the fixing parts 3 are transferred and affixed to respective side edges of the diaper main-body base material 20. Referring to FIG. 15, the fixing part 3 is folded back so that a portion protruding from the base material 20 is located inside the base material 20. Then, an unnecessary portion of the fixing part 3 is cut out along the cutout line 41 together with part of the base material 10 as superimposed thereon. Concurrently with this, an unnecessary portion of the base material 20 is cut out along the cutout lines 42 to form leg openings of the diaper main body 2. With this, referring to FIG. 16, the fixing protrusions 31 and 32 are formed, and the movable parts 21 and 22 are formed in a suitable shape. Finally, the base material 20 is cut in the width direction to form separate and distinct diaper 1.

According to the third embodiment, no S-shaped cutter is needed, and only one tape transfer device is needed with respect to each side edge of the diaper main-body base material 20, allowing curtailment of capital investment. On the other hand, the unnecessary portion to be cut out and discarded is greater than that in the first and second embodiments, raising a problem of increasing material cost. The strength of attachment for adaptation to target animals can be adjusted by arbitrarily changing the cutter size in accordance with the length of the fixing part. When firm fixing about the legs is desired, for example, the cut length about the legs can be increased.

In the third embodiment, the base materials 15A and 15B of the fastening member 15 are continuously formed as shown in FIG. 13. Optionally, referring to FIG. 17, the base materials 15A and 15B may be formed of previously cut portions so as to merely be mounted at required positions. With this, the usage of the fastening member 15 can be reduced.

Component Materials

The fixing part is composed of a resin film, unwoven fabric, laminate of resin film and unwoven fabric, or the like. One of the joining tape and the fastening member is formed with a plurality of hook-like or mushroom-like protrusions, whereas the other is formed with a plurality of engaged portions such as loops with which the protrusions are engaged. Such a structure is referred to as Velcro (trade name). An alternative may be adopted in which the fixing protrusions 31 and 32 are composed of an adhesive tape, and the fastening member 15 includes an adhesive layer. In this alternative, the first and second joining tapes 5 and 6 are composed, preferably, of a resin film. Moreover, a shearing force is, preferably, between 60 and 30 N, and more preferably, between 45 and 55 N.

While the preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. A method of manufacturing an absorbent article for an animal, the absorbent article including a fixing device for fixing a belly facing section applied to a belly of the animal and a back facing section applied to a back of the animal when the absorbent article is attached to the animal, the method comprising:

mounting an elongated fastening material to an elongated tape base material;

cutting the tape base material into separate and distinct fixing parts, each said fixing part including a pair of fixing protrusions each having thereon a fastening member defined by a piece of the fastening material, wherein the cutting defines a cut-out portion which has a bottom between the pair of fixing protrusions;

mounting at least one said fixing part to each side edge of the belly facing section, or each side edge of a sheet base material serving as a material of the belly facing section or the back facing section, wherein said fixing protrusions project outwardly beyond an associated side edge of the belly facing section or the sheet base material and said bottom of the cut-out portion lies inward of the associated side edge of the belly facing section or the sheet base material; and cutting away, together with the fixing part, a portion of the belly facing section or the sheet base material that have the fixing part mounted thereto, thereby said fixing protrusions of the fixing part are entirely separated from each other, wherein the tape base material has a first side edge extending in a length direction of the tape base material and a second side edge opposite to the first side edge in a width direction of the tape base material;

wherein the cutting of the tape base material comprises a first cutting process of cutting the tape base material along a first meandering cutting line continuously extending in the length direction with peaks and valleys, said peaks being adjacent to the first side edge of the tape base material and said valleys being adjacent to the second side edge of the tape base material; and a second cutting process of cutting the tape base material along second cutting lines each extending from the first side edge of the tape base material to one of the valleys or from the second side edge of the tape base material to one of the peaks so as to obtain said separate and distinct fixing parts serving as fastening tapes, wherein the second cutting lines define opposite ends, in the length direction of the tape base material, of the fixing parts, and dimensions of the ends of the fixing parts in the width direction of the tape base material are the maximal distances between the first cutting line and the side edges of the tape base material.

2. The method as claimed in claim 1, wherein said first cutting line has an amplitude between each valley and an adjacent peak greater than a width of the fastening material in the width direction of the tape base material.

3. The method as claimed in claim 2, further comprising adjusting a timing of the second cutting process so as to allow individual adaptation of the fixing device of the absorbent article to an animal that is to wear the absorbent article.

4. The method as claimed in claim 3, wherein a dimension of the fixing part in the length direction of the sheet base material is 40 to 200 mm.

5. The method as claimed in claim 3,
wherein said adjusting comprises adjusting at least one of the second cutting lines so that one of the fixing protrusions of each said fixing part is wider, in the length direction of the tape base material, than the other,
wherein both said fixing protrusions of each said fixing part are attached to the belly facing section of an individual absorbent article.

6. The method as claimed in claim 2, wherein a dimension of the fixing part in the length direction of the sheet base material is 40 to 200 mm.

7. The method as claimed in claim 1, wherein said cutting away is performed between the pair of fixing protrusions of each said fixing part.

8. The method as claimed in claim 1, wherein said second cutting process comprises cutting the tape base material, along each of the second cutting lines, from the first or second side edge of the tape base material, and through an entire width of the fastening material.

9. The method as claimed in claim 1, wherein said second cutting line extend lines extend perpendicular to the first and second side edges of the tape base material.

10. The method as claimed in claim 1, wherein
the portion cut away from the side edge of the belly facing section or the sheet base material is cut away together with a portion from the mounted fixing part, and
the portion cut away from the side edge of the belly facing section or the sheet base material is greater than the portion cut away from the mounted fixing part.

11. The method as claimed in claim 1, wherein
the fixing part further includes a straight side edge opposing to the bottom of the cut-out portion, and
the cutting and separating is along a cutout line that extends inwardly beyond the straight side edge of the fixing part.

* * * * *